United States Patent [19]

Sargenti

[11] 4,381,917

[45] May 3, 1983

[54] GUIDE ACCESSORY FOR A DRILL MOUNTED ON DENTAL HAND-TOOL

[75] Inventor: Angelo Sargenti, Locarno, Switzerland

[73] Assignee: Micro-Mega S.A., Besancon, France

[21] Appl. No.: 348,602

[22] Filed: Feb. 12, 1982

[51] Int. Cl.³ .......................... A61C 1/10; A61C 3/00
[52] U.S. Cl. ...................................... 433/114; 433/72
[58] Field of Search ...................... 408/67, 95, 97, 98; 433/72, 114

[56] References Cited

FOREIGN PATENT DOCUMENTS 2399297 4/1979 France .................................. 408/97

Primary Examiner—Robert Peshock
Attorney, Agent, or Firm—Prutzman, Kalb, Chilton & Alix

[57] ABSTRACT

It consists of a movable guide (3) surrounding the drill and attached to the head of the hand-tool by way of elastic means able to be compressed, the frontal portion (7) of the said guide (3) during the whole duration of the drilling being applied against the gum which it compresses, and the guide including a bore through it for the drill (2) to pass through.

8 Claims, 3 Drawing Figures

FLIPPER CONTROL CIRCUIT, PINBALL LOGIC BOARD SECTION

FIG. 1   FLIPPER CONTROL CIRCUIT, PINBALL LOGIC BOARD SECTION

GUIDE ACCESSORY FOR A DRILL MOUNTED ON DENTAL HAND-TOOL

The object of the invention is a guide accessory for a drill mounted on a dental hand-tool and employed essentially for drilling through the bony cortex of the jaw.

At the time of his operations the dental surgeon nowadays is confronted with the problem of having to drill through the bony cortex of the jaw in order to reach the central portion of the bone. This is quite particularly the case in order to carry out anaesthesia. Before reaching the cortex proper with the drill it is necessary first of all to pass through the gum. Very severe problems are posed at this level.

That is, the gum has a fibrous structure. At the first contact of the drill with the latter a fibre catches on a lip of the drill and wraps itself around the rotating stem of the drill. Thus there is a risk of tearing a whole shred of flesh several centimetres long and leading to veritable mulilation of the patient.

On the other hand if the drill is long, when the end of it comes into contact with the bone whilst revolving it is thrown sideways and the drill is twisted without the dental surgeon having time to take it into account and to react. There is then a double risk of breakage and of tearing of the soft tissues.

The object of the present invention is to palliate these several disadvantages of the known devices.

In accordance with the invention this result is obtained with a guide accessory for a drill mounted on a dental hand-tool and employed essentially for drilling through the bony cortex of the jaw, characterized in that it consists of a movable guide surrounding the drill and attached to the head of the hand-tool by way of elastic means able to be compressed, the frontal portion of the said guide during the whole duration of the drilling being applied against the gum which it compresses, and the guide including a bore through it for the drill to pass through.

It will easily be understood that in the uncompressed position the assembly of the guide and its elastic supporting means is longer than the useful length of the drill, so that in the position of rest the drill does not therefore project with respect to the plane of the front face of the guide. It is only when pressure is exerted upon the elastic means by applying the guide against the gum and bearing down on the hand-tool that the drill comes to pass beyond the guide and to penetrate the compressed gum. Because of the compression there is no longer any tearing of the fibres of the gum. That is, the fibres which might adhere to the lips of the drill are wedged between the bone and the guide and break without being able to wrap themselves round the drill.

This guide may be mounted removeably or difinitely on the head of the hand-tool.

The invention will be better understood thanks to the description below of a preferred embodiment, by reference to the attached drawings in which:

FIG. 4 is a view of the device in accordance with the invention in an intermediate position during the course of operation.

Figure 1:
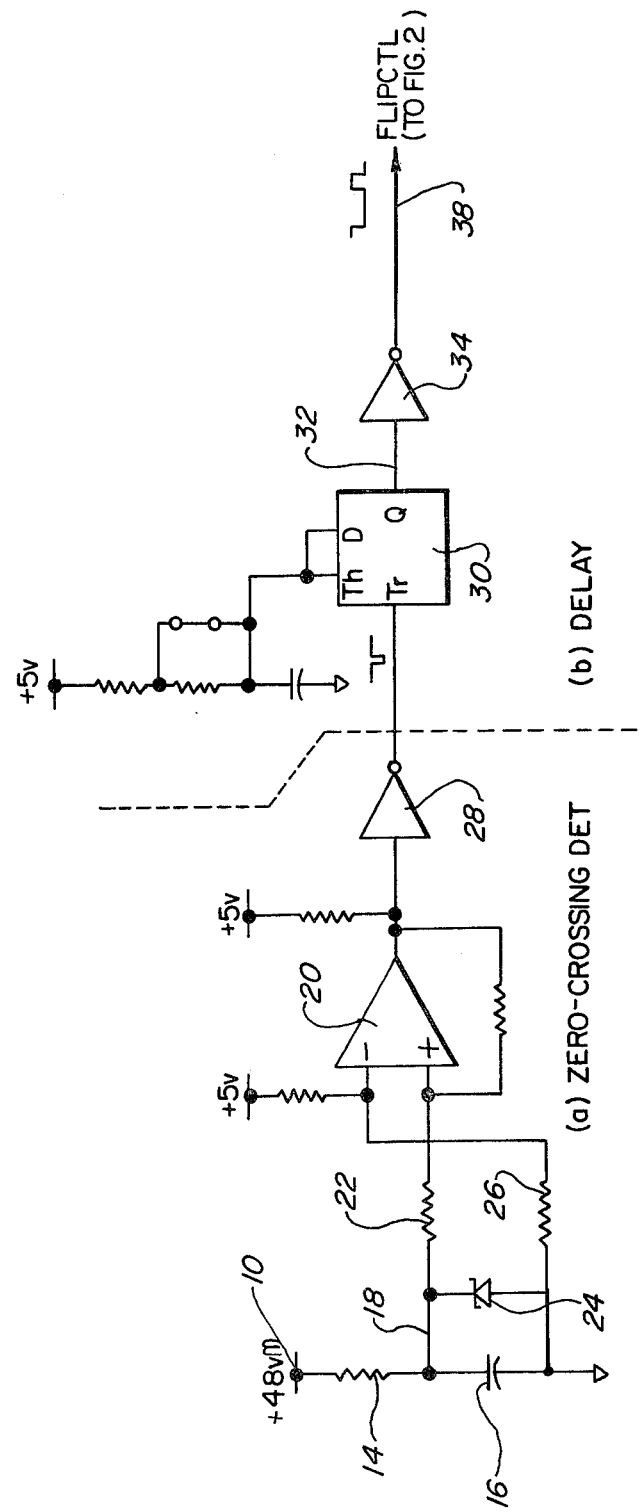
FIG. 1 is a view of a conventionally equipped cranked head of a drill.

In FIG. 1 there is shown a cranked head (1) the actual type of which is immaterial and which furthermore may possibly be a righthanded tool. Upon the cranked head is mounted a drill (2) endowed in known manner with a rotary motion. This representation in fact illustrates clearly the prior art.

Figure 2:
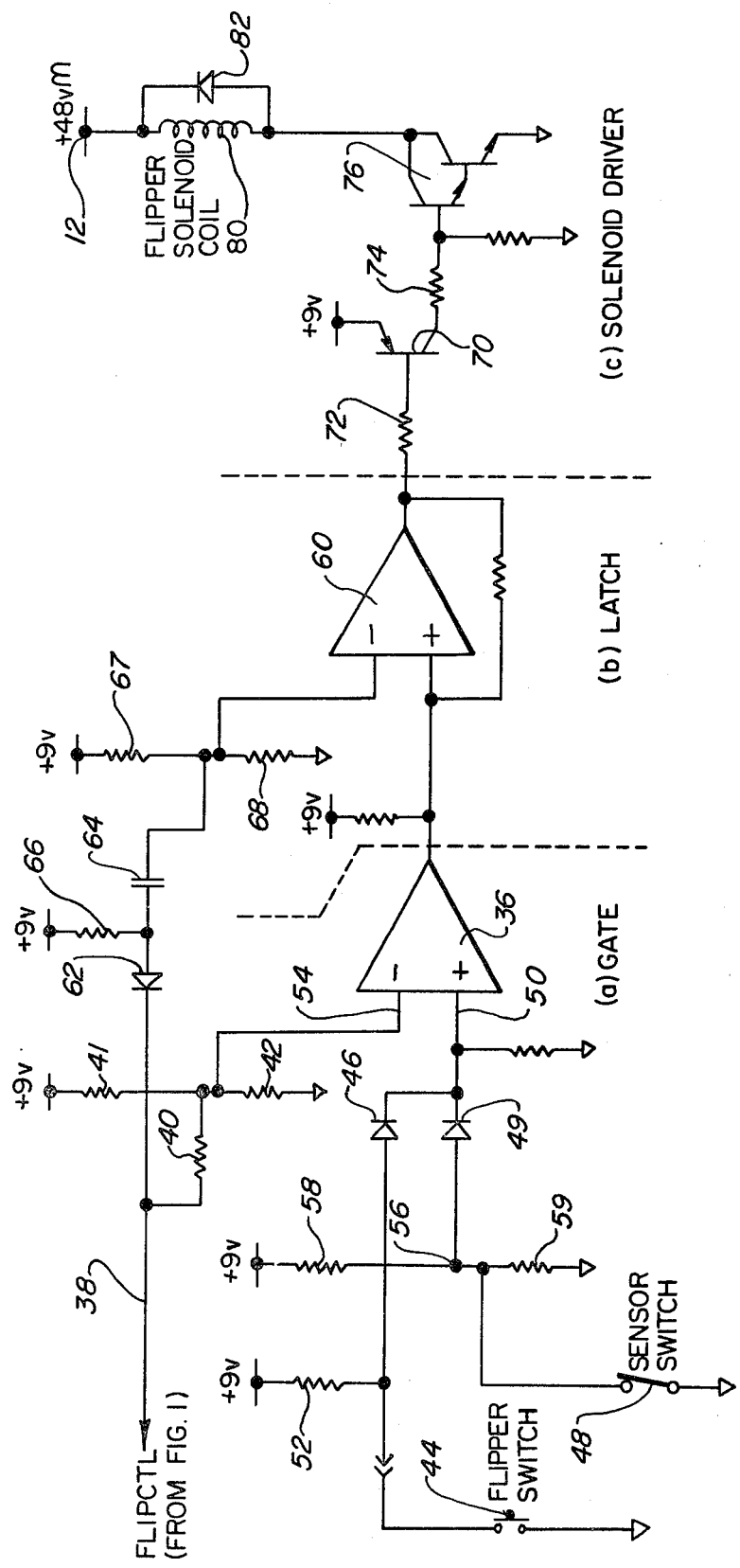
FIG. 2 is a view of removeable guide which can be fitted onto the cranked head as FIG. 1.

In FIG. 2 is shown an accessory in accordance with the invention consisting essentially of a barrel guide (3) attached to one of the ends of a spiral spring (4) which in turn is attached at the other end of it to an attachment claw (5). The guide (3) is the general shape of a truncated cone and includes a central bore (6) passing through it.

Figure 3:
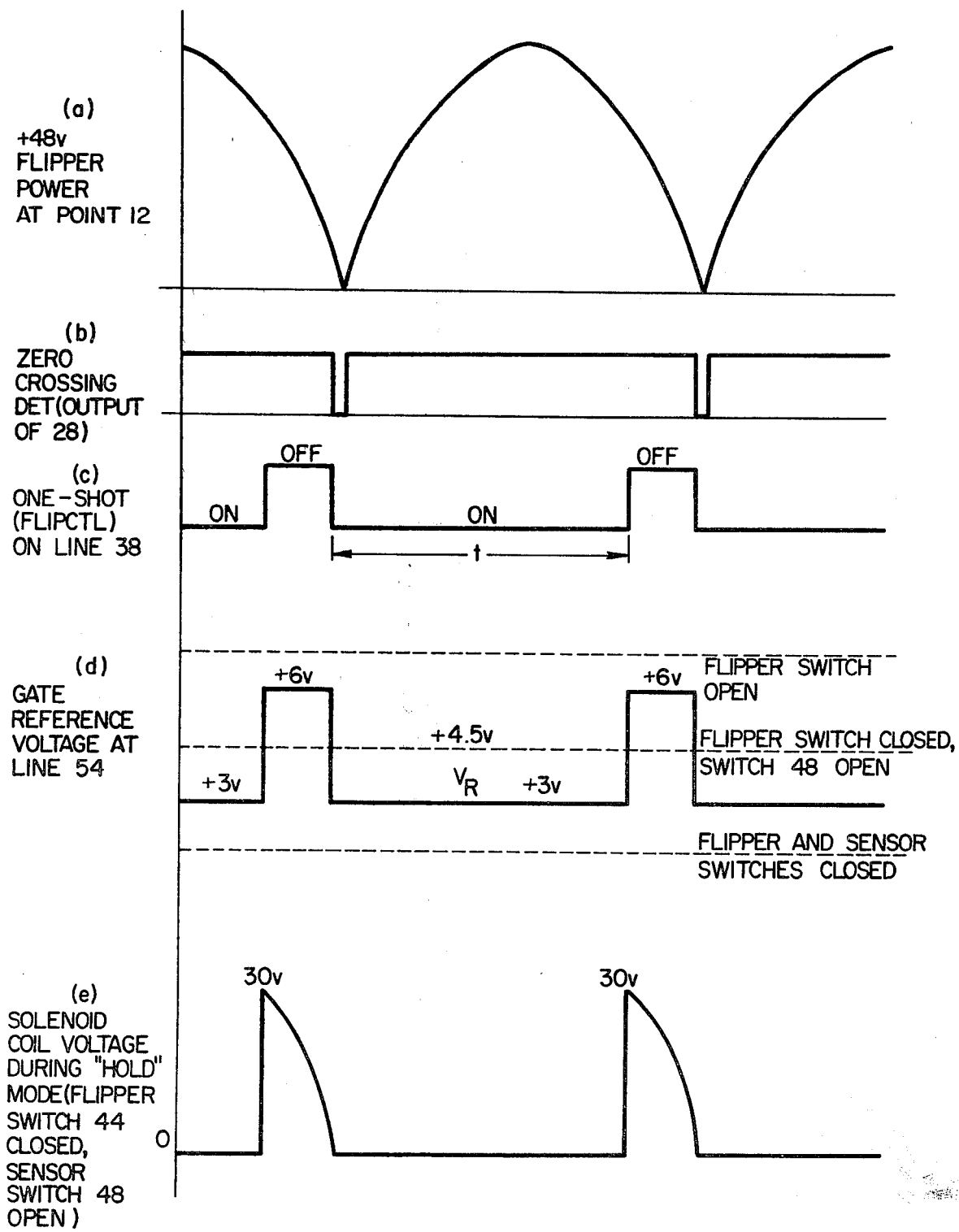
FIG. 3 is a view of the removeable guide as FIG. 2, positioned on the cranked head as FIG. 1.

In the position ready for use, shown in FIG. 3, the accessory is attached to the head of the crank by way of the claw (5) or of course by an equivalent means of attachment. As indicated previously, the assembly may equally well be attached definitely to the cranked head. It may be seen in FIG. 3 that the drill (2) does not project with respect to the front plane (7) of the guide (3).

When it is desired to drill through the gum of a patient, the face (7) of the guide (3) is applied to the gum and a pressure is exerted upon the cranked head, tending the make the spring (4) contract. As soon as the tip of the drill is flush with the plane (7) drilling starts. If pressure is continued against the cranked head drilling starts and the drill penetrates as required into the gum, the spring (4) being compressed more and more. In FIG. 4 an intermediate position is shown diagrammatically, with the gum (8) and the front end of the drill (2) which has penetrated into it.

The diameter of the bore (6) in the barrel guide (3) is slightly greater than the maximum diameter of the drill.

The drill may be of any type, either very fine for the passage of a needle for anaesthesia, or larger with a view to apical resection.

Hence it will be understood that the function of the guide (3) is a double one:

to compress the tissues of the gum so as to avoid tearing;

guidance of the drill at a certain distance from the head of the hand-tool, thus averting the risk of its twisting.

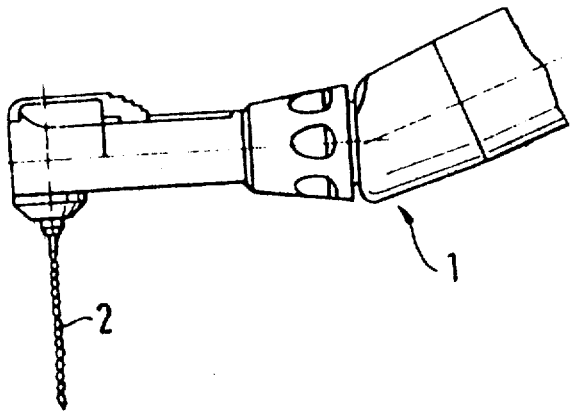

Fig.1
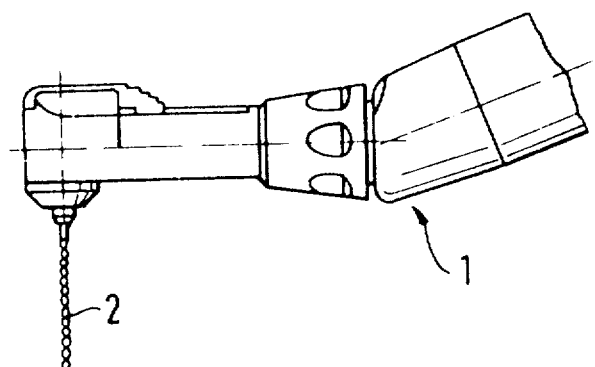
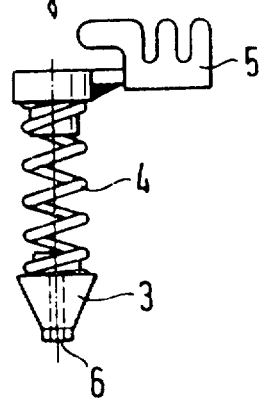
Fig.2
Fig.3
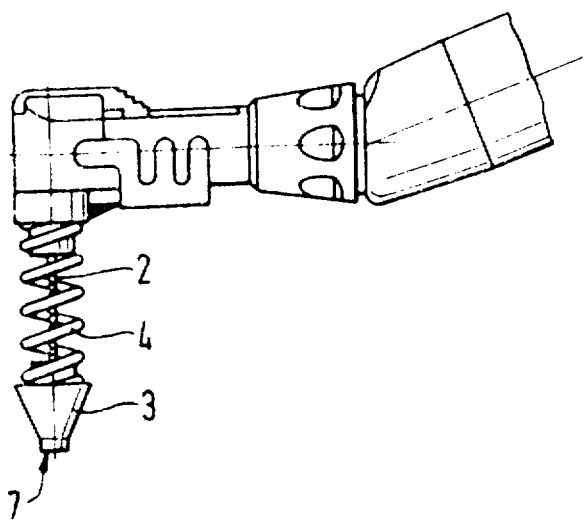
Fig.4
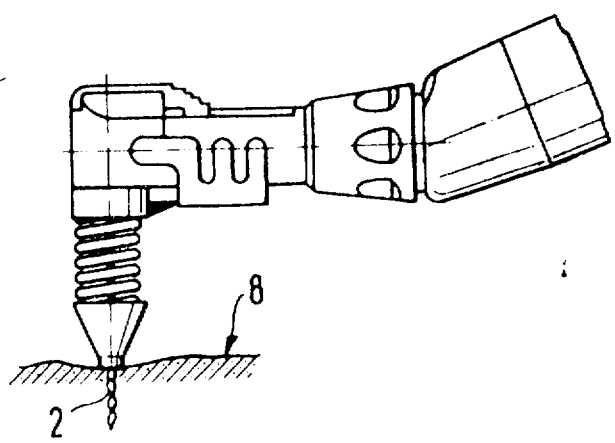

I claim:

1. A tissue stabilizing accessory for a dental hand drill having a drill bit and employed essentially for drilling through the gum and bony cortex of the jaw comprising:

a mounting member for fixedly securing the accessory to the dental drill for non-rotatable movement therewith;

compression spring means fixedly supported on said mounting member for coaxial alignment with the drill bit in spaced relationship thereto and;

a tissue compressing pressure foot fixedly mounted on said spring means remote from said mounting member and having a tissue contacting face for engagement with the gum and an axial bore only slightly larger in diameter than the drill bit and extending centrally through said face, said pressure foot being configured so as to impart controlled pressure through said compression spring means to the gum engaged by the tissue contacting face adjacent said bore.

2. The tissue stabilizer of claim 1 wherein the tissue compressing pressure foot is positioned in aligned spaced relationship to said mounting member by said spring means and is adapted for movement toward said mounting member against the bias of said spring means and away from said mounting means toward a rest position.

3. The tissue stabilizing accessory of claim 1 wherein the tissue compressing pressure foot is provided with a truncated cone configuration tapering toward said tissue contacting face for concentrating the controlled pressure on the tissue engaged by said face.

4. The tissue stabilizing accessory of claim 1 wherein said compression spring means is of sufficient length at rest so as to place the tissue contacting face of the pressure foot beyond the free end of the drill bit and permit engagement of the face with the gum tissue to provide compression of the gum tissue before contact by the drill bit.

5. The tissue stabilizing accessory of claim 1 wherein the compression spring means includes a compression coil spring extending longitudinally from said mounting member to said pressure foot whereby the drill bit extends along the axis of the coil spring for alignment with the axial bore in the pressure foot.

6. The tissue stabilizing accessory of claim 1 wherein the mounting member includes an attachment claw.

7. A method of stabilizing gum tissue and guiding the drill bit of a dental drill when drilling through the gum and bony cortex of the jaw comprising the steps of:
providing a tissue stabilizing accessory for a dental drill comprising a mounting member, a tissue compressing pressure foot, and compression spring means interconnecting said pressure foot and said mounting member, said foot having a tissue contacting face and a central bore extending therethrough to permit passage of the dental bit therethrough for drilling;
mounting the accessory on the dental drill for non-rotatable movement therewith;
engaging the tissue with said tissue contacting face;
extending the drill bit through the bore while compressing the contacted tissue and maintaining the compression on said tissue while drilling.

8. The method of claim 7 wherein said pressure foot has a truncated cone configuration and moves toward said mounting member against the bias of said compression spring means, including the step of concentrating the compression on the contacted tissue adjacent the bore by applying compressive force through the truncated cone shaped pressure foot to the tissue contacting face against the bias of the compression spring means.

* * * * *

UNITED STATES PATENT AND TRADEMARK OFFICE
CERTIFICATE OF CORRECTION

PATENT NO. : 4,381,917
DATED : May 3, 1983
INVENTOR(S) : Angelo Sargenti

It is certified that error appears in the above-identified patent and that said Letters Patent is hereby corrected as shown below:

The title page should be deleted to appear as per attached title page.

Sheets 1, 2 and 3 of the drawings should be deleted to appear as per attached sheet.

On the title page, "8 Claims, 3 Drawing Figures" should read -- 8 Claims, 4 Drawing Figures --.

Signed and Sealed this

Twenty-seventh Day of September 1983

[SEAL]

Attest:

Attesting Officer

GERALD J. MOSSINGHOFF

Commissioner of Patents and Trademarks

United States Patent [19]

Sargenti

[11] 4,381,917
[45] May 3, 1983

[54] GUIDE ACCESSORY FOR A DRILL MOUNTED ON DENTAL HAND-TOOL

[75] Inventor: Angelo Sargenti, Locarno, Switzerland

[73] Assignee: Micro-Mega S.A., Besancon, France

[21] Appl. No.: 348,602

[22] Filed: Feb. 12, 1982

[51] Int. Cl.³ .......................... A61C 1/10; A61C 3/00
[52] U.S. Cl. ...................................... 433/114; 433/72
[58] Field of Search .................. 408/67, 95, 97, 98; 433/72, 114

[56] References Cited

FOREIGN PATENT DOCUMENTS 2399297  4/1979  France ......................... 408/97

Primary Examiner—Robert Peshock
Attorney, Agent, or Firm—Prutzman, Kalb, Chilton & Alix

[57] ABSTRACT

It consists of a movable guide (3) surrounding the drill and attached to the head of the hand-tool by way of elastic means able to be compressed, the frontal portion (7) of the said guide (3) during the whole duration of the drilling being applied against the gum which it compresses, and the guide including a bore through it for the drill (2) to pass through.

8 Claims, 3 Drawing Figures